United States Patent [19]

Becker et al.

[11] Patent Number: 5,352,769

[45] Date of Patent: Oct. 4, 1994

[54] ENZYMATIC REMOVAL OF A PROTEIN AMINO-TERMINAL SEQUENCE

[75] Inventors: Gerald W. Becker; Thomas C. Furman; Warren C. MacKellar; James P. McDonough, all of Indianapolis, Ind.

[73] Assignee: Eli Lilly and Company, Indianapolis, Ind.

[21] Appl. No.: 864,098

[22] Filed: Apr. 6, 1992

Related U.S. Application Data

[62] Division of Ser. No. 349,472, May 9, 1989, Pat. No. 5,126,249.

[51] Int. Cl.$^5$ .................. C07K 7/40; A61K 37/26
[52] U.S. Cl. .................. 530/303; 530/305; 435/68.1
[58] Field of Search .............. 530/303, 402; 435/68.1, 435/69.1, 69.4; 514/3

[56] References Cited

U.S. PATENT DOCUMENTS

4,946,828  8/1990  Markussen .
5,164,366  11/1992  Balschmidt et al. .

FOREIGN PATENT DOCUMENTS

0383472A2  2/1990  European Pat. Off. .
WO86/01299  2/1986  PCT Int'l Appl. .
WO86/04609  8/1986  PCT Int'l Appl. .

OTHER PUBLICATIONS

J. K. McDonald et al., *Tissue Proteinases*, A. J. Barrett and J. T. Dingles, Eds., North-Holland Publishing Co., Amsterdam, 69-107 (1971).

J. K. McDonald et al., *Proteinases in Mannalian Cells and Tissues*, A. J. Barrett, Ed. Elsevier/North-Holland Biomedical Press, New York, 311-322 (1977).

J. K. McDonald et al., *Methods in Enzymology*, 25, C. H. W. Hirs and S. N. Timasheff, Eds. Academic Press, New York, 272-281 (1972).

Hsiung, et al., "Expression of Bovine Growth Hormone Derivatives in *Escherichia coli* and the Use of the Derivatives to Produce Natural Sequence Growth Hormone by Cathepsin C Cleavage, Methods in Enzymology", 153: 390-401 (1987).

G. T. Burke et al., *Biochemical and Biophysical Research Communications*, 173:3, 982-987 (1990).

*Primary Examiner*—George C. Elliott
*Attorney, Agent, or Firm*—Ronald S. Maciak; Paul R. Cantrell

[57] ABSTRACT

This disclosure relates to new compounds and to a process for the controlled conversion of such compounds to produce a Protein that comprises an amino acid sequence which is useful as a precursor to human insulin or to a modified human insulin, the amino terminus portion of which sequence does not define a cathepsin C dipeptide removal stop point. The compounds have the formula Met-Y-Protein in which Y is Tyr or Arg.

10 Claims, No Drawings

ENZYMATIC REMOVAL OF A PROTEIN AMINO-TERMINAL SEQUENCE

This application is a division of application Ser. No. 07/349,472, filed May 9, 1989, now U.S. Pat. No. 5,126,249.

BACKGROUND OF THE INVENTION

The biosynthesis of proteins in genetically altered procaryotic cells generally results in expression of a protein having a methionine attached at the amino terminus. Since the addition of methionine to the native protein may alter its biological activity, conformational stability, antigenicity, etc., it is most desirable, if possible, to remove it.

By insertion of a cleavage site between the amino-terminal methionine and the desired native peptide, one in theory has a greater degree of flexibility in the methodology selected for achieving production of the desired native peptide. In fact, however, there have been only a very limited number of practical methods for achieving selective cleavage.

For example, in those native proteins in which methionine is not present, cyanogen bromide mediated cleavage (methionine being the selective cleavage site) has proven to be a very effective method for generating the native protein. In fact, however, the absence of methionine is a rare occurrence in moderately-sized peptides and proteins. Furthermore, the serious toxicity of cyanogen bromide makes its use less than desirable and necessitates extreme caution in its handling. A most important objective thus is to discover alternate methods by which the amino-terminal methionine can be eliminated with generation of the native biosynthetically-produced protein.

One method recognized to be available for N-terminal methionyl removal involves the use of cathepsin C, also referred to as dipeptidyl-aminopeptidase 1 (DAP-1). Cathepsin C is an enzyme which removes two amino acids, as a unit, from the amino terminus of a protein or polypeptide. Under appropriate conditions, dipeptide removal will commence and continue unless and until (1) the amino group of the N-terminus amino acid is blocked, (2) the site of removal is on either side of a proline, or (3) the N-terminus amino acid is lysine or arginine.

Cathepsin C thus may have some usefulness in producing a desired biosynthetically-produced protein from a precursor molecule by designing such precursor molecule to contain an amino acid residue between the initiating methionine and the desired product. Treatment of the precursor molecule with cathepsin C can result in removal of the initiating dipeptide with production of the desired product. This process, however, may be severely limited in its application since dipeptide removal will be expected to continue sequentially until one of the aforedescribed termination sequences is reached. Thus, the cathepsin C approach should find limited usefulness, being applicable generally only in those instances in which the N-terminal portion of the desired product is itself a cathepsin C stop point.

It has now been discovered, however, that the identity of the N-terminal dipeptide of the precursor molecule plays a role in the degree to which dipeptide removal using cathepsin C can be controlled. It is this finding which forms the basis of this invention. Thus, it has been discovered that, when the initiating dipeptide is Met-Tyr or Met-Arg, dipeptide removal can be carefully controlled to obtain the desired product without further degradation occurring irrespective of whether the dipeptide next in the sequence is a cathepsin C stop point. It is to this discovery that the present invention is directed.

SUMMARY OF THE INVENTION

Thus, this invention is directed to a compound of the formula

Met-Y-Protein in which Protein comprises an amino acid sequence useful as a precursor to human insulin or to a modified human insulin, the amino terminus portion of which sequence does not define a cathepsin C dipeptide removal stop point, and Y is Tyr or Arg.

This invention also is directed to a process for producing a precursor to human insulin or to a modified human insulin, which comprises treating a compound of the formula Met-Y-Protein in which Protein comprises an amino acid sequence useful as a precursor to human insulin or to a modified human insulin, the amino terminus portion of which sequence does not define a cathepsin C dipeptide removal stop point, and Y is Tyr or Arg, in the presence of cathepsin C, chloride ion, and a compound which affords a sulfhydryl moiety.

DETAILED DESCRIPTION OF THE INVENTION

As noted, this invention is directed to compounds which include a moiety designated as Protein. The Protein comprises an amino acid sequence that is useful as a precursor to human insulin or to an analog of human insulin and the amino terminus portion of which sequence does not define a natural stop point for dipeptide removal using cathepsin C. In general, this sequence will be composed of three amino acid sequence units, designated, in order, beginning at the N-terminal, B, X, and A. The Sequence designated "B" represents the B-chain of human insulin or a modified B-chain. The sequence designated "A" represents the A-chain of human insulin or a modified A-chain. By "modified B-chain" or "modified A-chain" is meant an amino acid sequence which, when joined by disulfide bond linkage to the native or to a modified form of the other chain, gives rise to a molecule having insulin-like properties.

The group X represents a moiety which is joined to the insulin A-chain or modified A-chain at the amino terminus of the A-chain and to the insulin B-chain or modified B-chain at the carboxy terminus of the B-chain. The connecting moiety, X, of the precursor can be any of a wide range of polypeptide structures. The polypeptide generally has at least 2 and, preferably, from about 2 to about 35 and, most preferably, from about 6 to about 35 amino acid residues. Most preferably, the connecting moiety, X, when it is a peptide, is the natural connecting peptide of human proinsulin, such connecting peptide having the formula:

—Arg—Arg—Glu—Ala—Glu—Asp—Leu—Gln—Val—Gly—

Gln—Val—Glu—Leu—Gly—Gly—Gly—Pro—Gly—Ala—

-continued

Gly—Ser—Leu—Gln—Pro—Leu—Ala—Leu—Glu—Gly—

Ser—Leu—Gln—Lys—Arg—.

Although it is preferred that X be the natural connecting sequence, as indicated above, X can be any of a wide range of shorter peptide sequences. The only requirements are (1) that the sequence be of sufficient length to permit proper disulfide bond formation between the A- and B-chains, and (2) that it be cleavable from the insulin or modified insulin precursor with accompanying insulin or modified insulin formation. A typical dipeptide for X can be -Arg-Arg-. In addition, X can be an extension of the foregoing dipeptide, namely those sequences having the formula -Arg-X'-Arg- in which X' represents at least one amino acid residue. Highly preferred connecting peptides are -Arg-Arg-Lys-Arg- as well as longer chain peptides having the structure -Arg-Arg-$X^2$-Lys-Arg- in which $X^2$ is at least one amino acid residue and preferably at least two amino acid residues. These latter, of course, include the natural connecting peptide.

In native human insulin, the B-chain has the following sequence:

Phe—Val—Asn—Gln—His—Leu—Cys—Gly—Ser—His—Leu—Val—
 1    2    3    4    5    6    7    8    9    10   11   12

Glu—Ala—Leu—Tyr—Leu—Val—Cys—Gly—Glu—Arg—Gly—Phe—Phe—
 13   14   15   16   17   18   19   20   21   22   23   24   25

Tyr—Thr—Pro—Lys—Thr.
 26   27   28   29   30

Highly preferred in the compounds of this invention is the native human B-chain sequence. Also preferred, however, are those sequences containing, independently, one or more of the following amino acid modifications:

(1) replacement of the Pro in position 28 by any of the following: Asp, Val, Leu, Ile, Nle, Arg, His, Lys, Phe, Ala, Gly, citrulline, and ornithine. Of these replacements, the following are more preferred: Val, Leu, Ile, Nle, Arg, His, Lys, and ornithine; and, of these, Lys is most preferred.

(2) replacement of the Lys in position 29 by any of the following: L-Pro, D-Pro, D-hydroxyproline, L-hydroxyproline, L-(N-methyl)Lys, D-Lys, L-(N-methyl)Arg, and D-Arg. Of these replacements, L-Pro is most preferred.

(3) replacement of the His in position 10 by Asp.

(4) deletion of the Thr in position 30.

In native human insulin, the A-chain has the following sequence:

Gly—Ile—Val—Glu—Gln—Cys—Cys—Thr—Ser—Ile—Cys—Ser—
 1    2    3    4    5    6    7    8    9    10   11   12

Leu—Tyr—Gln—Leu—Glu—Asn—Tyr—Cys—Asn.
 13   14   15   16   17   18   19   20   21

Highly preferred in the compounds of this invention is the native human A-chain sequence. Also preferred, however, is that sequence in which the Asn in position 21 is replaced by Ala.

Throughout this specification conventional amino acid abbreviations are used and have the following meanings:

| Abbreviation | Amino Acid |
| --- | --- |
| Ala | Alanine |
| Arg | Arginine |
| Asn | Asparagine |
| Cys | Cysteine |
| Gln | Glutamine |
| Glu | Glutamic acid |
| Gly | Glycine |
| His | Histidine |
| Ile | Isoleucine |
| Leu | Leucine |
| Nle | Norleucine |
| Phe | Phenylalanine |
| Pro | Proline |
| Ser | Serine |
| Thr | Threonine |
| Tyr | Tyrosine |
| Val | Valine |

Compounds of this invention which represent Met-Tyr or Met-Arg extensions of precursors to human insulin or to analogs of human insulin are selectively converted to such precursors by treatment with cathepsin C. A brief description of the cathepsin C treatment follows.

Cathepsin C, in order to be activated, requires the presence of chloride ion ($Cl^-$). Thus, in the conversion of the compounds of this invention, $Cl^-$ is added to the medium. The amount of chloride ion can be minimal, even catalytic. Indeed, residual amounts present as the result of earlier treatment of the protein in the presence, for example, of sodium chloride have been seen to be entirely adequate. Thus, the presence of at least a trace amount of chloride ion is sufficient.

Likewise, since the process for converting the compounds of the present invention is enzymatic, a minor amount, relative to the Met-Y-Protein starting material, of cathepsin C is employed. In general, on a molar basis and relative to the protein substrate, the cathepsin C is present in a ratio of from about 1:1000 to about 1:100,000. Preferably, the ratio will be not greater than about 1:10,000, and, generally, from about 1:10,000 to about 1:70,000.

The reaction generally is conducted in an aqueous medium suitably buffered to obtain and maintain a pH of from about 2.5 to about 10. Preferably, the pH of the medium is slightly acidic to neutral, ranging from about 2.5 to about 7, and, most preferably, is from about 3.0 to about 6.0.

In some cases, a solubilizing agent such as urea, sodium dodecylsulfate, guanidine, and the like, may be employed.

Any of a wide range of buffering agents can be employed, the only requirement being their ability to generate a pH within the desired range. Examples of typical such buffering agents are sodium phosphate, sodium acetate, sodium citrate, potassium phosphate, potassium acetate, potassium citrate, and the like. Preferred buffering agents are sodium acetate and potassium acetate.

Conversion of the compounds of this invention further requires the presence of a reagent affording a sulfhydryl moiety. Typical such reagents are $\beta$-mercaptoethanol, dithiothreitol, dithioerythritol, $\beta$-mercaptoethylamine, cysteine, and the like. Sulfhydryl reagents preferred for use are $\beta$-mercaptoethanol, dithiothreitol, and cysteine, and, most preferably, cysteine.

The sulfhydryl reagent generally is present in the final reaction medium at a molar concentration of from about 0.1 mM to about 200 mM, preferably from about 1 mM to about 20 mM.

The reaction is carried out generally at a temperature of from about 15° C. to about 45° C. for a period of from about 1 hour to about 24 hours. Preferably, the temperature of reaction is from about 20° C. to about 45° C., and, most preferably, from about 22° C. to about 42° C., with the reaction proceeding for a period of from about 6 hours to about 20 hours.

The product that is produced from the compounds of this invention upon treatment with cathepsin C will have the structure designated "Protein" which represents a precursor to human insulin or to a human insulin analog.

The Protein, once generated by treatment of Met-Y-Protein with cathepsin C, is subjected to conditions which lead to proper disulfide bond formation (folding) of the molecule. The resulting folded precursor to human insulin or a human insulin analog generally is represented by a molecule which (1) contains the human insulin A-chain (or analog) and the human insulin B-chain (or analog), (2) has three disulfide bonds represented by a joining of the sulfurs of each of the Cys moieties located in the A- and B-chains at (a) A-6 and A-11, (b) A-7 and B-7, and (c) A-20 and B-19, respectively, and (3) has a removable connecting moiety which is joined to the insulin A-chain (or analog) at its amino group and to the insulin B-chain (or analog) at its carboxyl group.

Typical conditions for achieving folding of the Protein are dilution with water of a concentrated Protein solution in 20 mM Glycine, pH 9, to a final Protein concentration of 1 gm/L. After addition of cysteine-HCl to a final concentration of 1.25 mM, the pH is adjusted to 10.5–10.7 with NaOH, and the solution is incubated at 5° C. for up to about 16 hours.

The folded molecule can then be subjected to enzymatic treatment under which the connecting moiety is removed with formation of the desired human insulin or human insulin analog. Highly preferred conditions for effecting such cleavage are those well recognized in the art employing a combination of trypsin and carboxypeptidase B. This methodology was first recognized a number of years ago [see, e.g., Kemmler, W., Clark, J. L., Borg, J. and Steiner, D. F., Fed. Proc. 30 (1971) 1210; Kemmler, W., Peterson, J. D., and Steiner, D. F., J. Biol. Chem., 246 (1971) 6786–6791].

The compounds of this invention are prepared via recombinant DNA methodology. In their preparation, a nucleotide sequence coding for the desired compound is prepared using now-routine techniques for such synthesis. These methods generally involve preparation of oligonucleotides coding both for fragments of the desired coding sequence and for their complementary sequence thereof. The oligonucleotides are designed to provide overlap of one fragment of the coding sequence with two fragments of the complementary sequence and vice versa. The oligonucleotides are paired and joined, ultimately producing the desired gene sequence.

The sequence is inserted into a cloning vector at a location which permits the product for which it codes to be expressed. A suitable cloning vector contains at least a portion of an expression control sequence.

The following examples are provided as a means of illustrating the present invention. They are not to be construed as imposing a limitation thereon.

EXAMPLE 1

Cleavage of Unfolded Met-Tyr-Proinsulin

Lyophilized Met-Tyr-proinsulin (cysteinyl form, 36% purity) was dissolved in 0.25N acetic acid, 7M urea to a final total protein concentration of 4.68 mg/ml (A276, E=1). This solution was diluted two-fold with 0.25N acetic acid. To 334 $\mu$l of this dilution was added 290 $\mu$l of 0.25N acetic acid, 7M urea, 136 $\mu$l of 0.25N acetic acid, and 40 $\mu$l of 1M NaH$_2$PO$_4$ for a final volume of 0.8 ml. The pH of this solution was adjusted to 6.0 using 5N NaOH. A DAP-1/cysteine/NaCl solution was prepared by mixing 400 $\mu$l of 1M NaCl, 250 $\mu$l of 100 mM cysteine HCl (pH 6 in H$_2$O), and 400 $\mu$l of a 1.93 unit/ml DAP-1 solution in 50 mM citrate, 10 mM NaCl at pH 5. DAP-1/cysteine/NaCl solution (53 $\mu$l) was mixed with 375 $\mu$l of the Met-Tyr-proinsulin dilution and incubated at room temperature (22° C.) for 30 minutes (final DAP-1/Met-Tyr-proinsulin=120 U/g). The reaction was quenched with six volumes of sulfitolysis reagent (7M urea, 0.5M Tris pH 8.5, 0.2M Na$_2$SO$_3$, 0.01M K$_2$S$_4$O$_6$) and analyzed by reversed-phase HPLC. Under these conditions quantitative conversion of Met-Tyr-proinsulin mixed disulfide to proinsulin S-sulfonate was achieved.

EXAMPLE 2

Cleavage of Unfolded Met-Tyr-Proinsulin Analog (B28 Lys, B29 Pro)

Met-Tyr-proinsulin analog (B28 Lys, B29 Pro) was produced as an insoluble protein in the cytoplasm of E. coli. The insoluble protein was isolated by cellular disruption and differential centrifugation. Solubilization was effected by transient pH elevation to 11.5 (10 minutes) in 7M urea, 5 mM cysteine followed by incubation at pH 8.9. The protein was purified by cation exchange chromatography in 50 mM acetic acid, 7M urea, pH 4 with a linear gradient in NaCl. This preparation (1.5 to 1.7 mg/ml in proinsulin analog at 30–50% OD purity) was adjusted to pH 5.7 using 6N NaOH. An aliquot (1.5 ml) of the solution was added to 1.35 ml of pH 5.7 buffer (50 mM acetic acid, 50 mM NaH$_2$PO$_4$), 0.075 ml of 200 mM cysteine (in pH 5.7 buffer), and 0.075 ml of 7.76 unit per ml DAP-1 (in pH 5.7 buffer). The mixture was incubated at room temperature (22° C.) for 0.7 to 20 hrs. The reaction was quenched with nine volumes of sulfitolysis reagent (75 urea, 0.55 Tris pH 8.5, 0.2M Na$_2$SO$_3$, 0.01M K$_2$S$_4$O$_6$) and analyzed by reversed-phase HPLC. Under these conditions 80–86% conversion of Met-Tyr-proinsulin analog mixed disulfide to the proinsulin analog S-sulfonate was achieved with undetectable degradation of the product by further enzymatic cleavage.

EXAMPLE 3

Cleavage of Unfolded Met-Arg-Proinsulin Analog (B28 Lys, B29 Pro)

Met-Arg-proinsulin analog (B28 Lys, B29 Pro) was produced as an insoluble protein in the cytoplasm of *E. coli*. The insoluble protein was isolated by cellular disruption and differential centrifugation. Solubilization was effected by transient pH elevation to 11.5 (10 minutes) in 7M urea, 5 mM cysteine followed by incubation at pH 8.9. The protein was purified by cation exchange chromatography in 50 mM acetic acid, 7M urea, pH 4 with a linear gradient in NaCl. This preparation (1.5 to 1.7 mg/ml in proinsulin analog at 30–50% OD purity) was adjusted to pH 5.7 using 6N NaOH. An aliquot (1.5 ml) of the solution was added to 1.35 ml of pH 5.7 buffer (50 mM acetic acid, 50 mM $NaH_2PO_4$), 0.075 ml of 200 mM cysteine (in pH 5.7 buffer), and 0.075 ml of 7.76 unit per ml DAP-1 (in pH 5.7 buffer). The mixture was incubated at room temperature (22° C.) for 0.7 to 20 hrs. The reaction was quenched with nine volumes of sulfitolysis reagent (7M urea, 0.5M Tris pH 8.5, 0.2M $Na_2SO_3$, 0.01M $K_2S_4O_6$) and analyzed by reversed-phase HPLC. Under these conditions 80–86% conversion of Met-Arg-proinsulin analog mixed disulfide to the proinsulin analog S-sulfonate was achieved with undetectable degradation of the product by further enzymatic cleavage.

We claim:

1. A compound of the formula Met-Y-Protein in which Protein comprises three amino acid sequence units designated B, A, and X, in which B represents the B-chain of human insulin or a modified B-chain having one or more of the following amino acid modifications:

(1) replacement of the Pro in position 28 by any of the following: Asp, Val, Leu, Ile, Nle, Arg, His, Lys, Phe, Ala, Gly, citrulline, and ornithine;

(2) replacement of the Lys in position 29 by any of the following: L-Pro, D-Pro, D-hydroxyproline, L-hydroxyproline, L-(N-methyl)Lys, D-Lys, L-(N-methyl)Arg, and D-Arg;

(3) replacement of the His in position 10 by Asp;

(4) deletion of the Thr in position 30; A represents the A-chain of human insulin or a modified A-chain, in which the asparagine in position 21 is replaced by alanine; and X represents a moiety joined to the insulin A-chain or modified A-chain at the amino terminus of the A-chain and to the insulin B-chain or modified B-chain at the carboxy terminus of the B-chain, the amino terminus portion of which sequence does not define a cathepsin C dipeptide removal stop point, and Y is Tyr or Arg.

2. Compound of claim 1, in which Y is Tyr.

3. Compound of claim 1, in which Y is Arg.

4. Compound of claim 1, in which A is the A-chain of human insulin.

5. Compound of claim 1, in which B is the B-chain of human insulin.

6. Compound of claim 1, in which X is the natural connecting peptide of human proinsulin.

7. Compound of claim 1, having a modified B-chain in which the Pro in position 28 has been replaced by Lys.

8. Compound of claim 1, in which the Lys in position 29 has been replaced by Pro.

9. Compound of claim 1, having a modified B-chain in which the Lys in position 29 has been replaced by Pro.

10. A compound of the formula

Met-Y-Protein in which Y is Arg and Protein is human proinsulin in which Pro at position 28 of the B-chain is replaced with Lys and in which Lys at position 29 of the B-chain is replaced with Pro.

* * * * *

UNITED STATES PATENT AND TRADEMARK OFFICE
CERTIFICATE OF CORRECTION

PATENT NO.   : 5,352,769

DATED        : October 4, 1994

INVENTOR(S)  : Gerald W. Becker; Thomas C. Furman;
               Warren C. MacKellar; James P. McDonough It is certified that an error appears in the above-identified patent and that said Letters Patent is hereby corrected as shown below:

Column 6, line 65, reads ..."(75 urea, 0.55 Tris pH 8.5, 0.2M $Na_2SO_3$, 0.01M $Na_2S_4O_6$)" ... should read --...(7$\underline{M}$ urea, 0.5$\underline{M}$ Tris pH 8.5, 0.2$\underline{M}$ $Na_2SO_3$, 0.01$\underline{M}$ $Na_2S_4O_6$)--

Column 8, line 29, "claim 1" should read --claim 7--.

Signed and Sealed this

Twenty-fourth Day of January, 1995

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,352,769
DATED : October 4, 1994
INVENTOR(S) : Gerald W. Becker, et al It is certified that error appears in the above-indentified patent and that said Letters Patent is hereby corrected as shown below:

On the title page item [56], "WO86/01299"...should read
--"WO86/01229"...--

Signed and Sealed this

Twenty-first Day of February, 1995

Attest:

BRUCE LEHMAN

Attesting Officer Commissioner of Patents and Trademarks